United States Patent [19]

Martin et al.

[11] 4,176,178
[45] Nov. 27, 1979

[54] 2-DEOXY-2'-N-ACYL AND ALKYL FORTIMICINS A AND B

[75] Inventors: Jerry R. Martin; John S. Tadanier, both of Waukegan; Paulette Collum, Zion, all of Ill.

[73] Assignee: Abbott Laboratories, North Chicago, Ill.

[21] Appl. No.: 863,011

[22] Filed: Dec. 21, 1977
(Under 37 CFR 1.47)

[51] Int. Cl.² .................. A61K 31/71; C07H 15/22
[52] U.S. Cl. ............................... 424/180; 536/4; 536/17 R
[58] Field of Search ..................... 424/180; 536/17

[56] References Cited
U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |

Primary Examiner—Johnnie R. Brown
Attorney, Agent, or Firm—Robert L. Niblack; Gildo E. Fato

[57] ABSTRACT

2-Deoxy-2'-N-acyl and alkyl fortimicin B and derivatives, 4,2'-N,N'-diacyl and dialkyl fortimicin B derivatives, 4-N-acyl-2'-N-alkyl- and 4-N-alkyl-2'-N-acyl fortimicin B derivatives represented by the formula

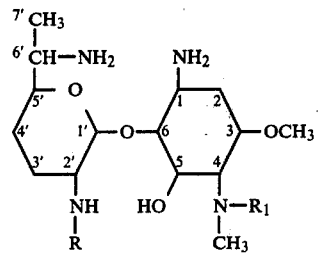

wherein R is acyl, aminoacyl, N-monoloweralkylaminoacyl, N,N-diloweralkylaminoacyl, hydroxy-substituted aminoacyl, hydroxyacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl or N,N-diloweralkylaminohydroxyloweralkyl; and $R_1$ is acyl, aminoacyl, N-monoloweralkylaminoacyl, N,N-diloweralkylaminoacyl, hydroxy-substituted aminoacyl, hydroxyacyl, an amino acid residue, loweralkylaminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, hydrogen; and the pharmaceutically acceptable salts therefor, pharmaceutical compositions containing the compounds and methods of making and using the compounds. The compounds of this invention are useful as antibiotics.

12 Claims, No Drawings

2-DEOXY-2'-N-ACYL AND ALKYL FORTIMICINS A AND B

BACKGROUND OF THE INVENTION

It is known that the antibacterial and pharmacological properties of many naturally produced aminoglycoside antibiotics can be altered by structural modifications. For example, certain chemical modifications in the gentamicin and kanamycin family of aminoglycoside antibiotics provide structures which are less toxic than the parent antibiotic. Further, in the same family series mentioned above, certain modifications alter the antibacterial spectrum advantageously either by increasing the intrinsic activity or increasing activity against resistant strains.

Historically, once an aminoglycoside antibiotic has been in clinical use for awhile, resistant microorganisms arise. In many cases, the resistance is R-factor mediated and is attributed to the ability of the bacteria to enzymatically modify the amino or hydroxyl groups of the aminoglycoside antibiotic. Thus there is a continuing need for new fortimicin aminoglycoside antibiotics.

The present invention provides new and useful fortimicin derivatives.

SUMMARY OF THE DISCLOSURE

2-Deoxy-2'-N-acyl and alkyl fortimicin B and fortimicin B derivatives, 4,2'-di-N-acyl and dialkyl, as well as 4-N-acyl-2'-N-alkyl and 4-N-alkyl-2'-N-acylfortimicin B derivatives are provided by this invention as well as their salts, intermediates, processes for making the compounds, and compositions and methods employing the compounds.

The fortimicin derivatives of this invention are antibiotics which are effective against various Gram-negative and Gram-positive bacteria and can be administered orally or parenterally in daily dosages of from about 1 to about 100 mg/kg of body weight daily to mammalian patients showing symptoms of infection caused by one of the susceptible bacteria.

The compounds can also be used as preservatives for various industrial solutions, in antibacterial scrub solutions for cleaning laboratory bench tops and the like. They are also useful as intermediates in preparing other useful fortimicin derivatives which have anti-bacterial activity.

The compounds of this invention are amines and form salts with fluosilicic acid which are useful as mothproofing agents according to the teachings of U.S. Pat. Nos. 1,915,334 and 2,075,359. They also form salts with thiocyanic acid which condense with formaldehyde to form resinous materials useful as pickling inhibitors as taught in U.S. Pat. Nos. 2,425,320 and 2,606,155.

Derivatives useful in the preparation of the compounds of this invention are provided as well as method of making and using the compounds and compositions employing the compounds.

DETAILED DESCRIPTION OF PREFERRED EMBODIMENTS

The present invention provides 2-deoxy-2'-N-acyl and alkyl fortimicin B derivatives, 2-deoxy-4,2'-di-N-acyl and dialkyl derivatives, 2-deoxy-4-N-acyl-2'-N-alkyl and 2-deoxy-4-N-alkyl-2'-N-acylfortimicin B derivatives represented by Formula I:

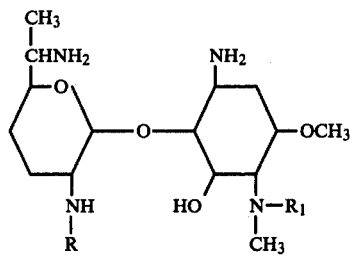

wherein R is acyl, aminoacyl, N-monoloweralkylaminoacyl, hydroxyacyl, N,N-diloweralkylaminoacyl, hydroxy-substituted aminoacyl, an amino acid residue, loweralkyl, aminoloweralkyl, hydroxyloweralkyl, aminohydroxyloweralkyl, N-loweralkylaminoloweralkyl, N,N-diloweralkylaminoloweralkyl, N-loweralkylaminohydroxyloweralkyl, N,N-diloweralkylaminohydroxyloweralkyl and $R_1$ is acyl, aminoacyl, N-monoloweralkylaminoacyl, N,N-diloweralkylaminoacyl, hydroxy-substituted aminoacyl, hydroxyacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen; and the pharmaceutically acceptable salts thereof.

The term "pharmaceutically acceptable salts" refers to non-toxic acid addition salts of the compounds of this invention which are generally prepared by reacting the base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

The term "acyl" refers to groups represented by the formula

wherein $R_1$ is loweralkyl, i.e., acetyl, propionyl, butyryl, etc.

"Lower alkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

The term "amino acid residue" refers to D, L or DL amino residues and includes, but is not limited to, glycyl, alanyl, sarcosyl, tyrosyl, phenylalanyl, methionyl, seryl, lysyl, asparaginyl, isoleucyl, leucyl, thereonyl, valyl, prolyl, glutaminyl, tryptophanyl, glutamyl and the like.

The 2'-N-acylfortimicin-2-deoxy B derivatives can be prepared by rearrangement of the corresponding 2-deoxy-4-N-substituted fortimicins B of Formula II, which are prepared from 2-deoxy-fortimicin B ($R_1$=H) and 2-deoxy fortimicin A ($R_1$=glycyl).

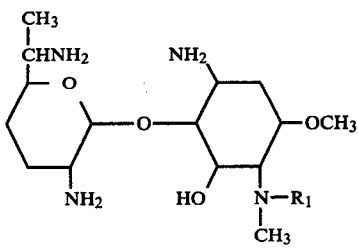

(II)

Fortimicin A and B are prepared according to the method of U.S. Pat. Nos. 3,976,768 and 3,931,400, respectively. The preparation of representative 2-deoxy-4-N-acylfortimicin B derivatives is set forth in the examples herein.

The intermediates of this invention are represented by Formula III

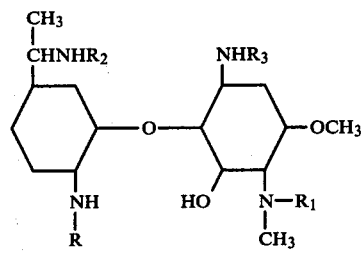

wherein R is as defined in Formula I or RZ wherein Z is benzyloxycarbonyl, $R_1$ is as defined in Formula 1 or RZ wherein Z is benzyloxycarbonyl, $R_2$ is hydrogen or benzyloxycarbonyl and $R_3$ is hydrogen or benzyloxycarbonyl with the limitation that $R_1$, $R_2$ and $R_3$ cannot each be hydrogen.

2-deoxy fortimicin B can be prepared as follows. In one process, fortimicin B, having all primary amino groups protected by benzyloxycarbonyl groups and the $C_5$ hydroxyl and $C_4$ secondary amino groups blocked by a suitable aldehyde to form an oxazolidine ring, upon treatment with a hydrocarbonsulfonyl halide or anhydride, is converted to a 2O-methanesulfonyl ester (e.g., to a 2-O-methanesulfonyl ester) which in turn is converted to a 1, 2′, 6′-tri-N-benzyloxycarbonyl-2-O-hydrocarbonsulfonyl ester derivative following acid hydrolysis of the oxazolidine ring, which is N-deblocked by catalytic hydrogenolysis in the presence of an acid. When the resulting 2-O-hydrocarbonsulfonylfortimicin B salt is converted to the free base, the intermediate 1,2-epiminofortimicin B is obtained. Continuing the process, catalytic hydrogenolysis of 1,2-epiminofortimicin B gives 2-deoxyfortimicin B which in turn is converted is 2-deoxyfortimicin A.

In an alternate procedure, the key intermediate 1,2-epiminofortimicin B is conveniently prepared as follows. Fortimicin B, having all primary amino groups protected by Schiff base formation from a suitable aldehyde (e.g., benzaldehyde) and the $C_5$ hydroxyl and $C_4$ secondary amino groups protected by the same aldehyde to form an oxazolidine ring, upon treatment with a hydrocarbonsulfonyl halide or anhydride, is converted to a 2-O-hydrocarbonsulfonyl ester which in turn is converted, on acid hydrolysis of the Schiff base and oxazolidene to a 2-O-hydrocarbonsulfonylfortimicin B salt. The salt upon conversion to the free base rearranges to 1, 2-epiminofortimicin B.

Continuing the process, catalytic hydrogenolysis of 1,2-epiminofortimicin B gives 2-deoxyfortimicin B which in turn is converted to the 1,2′,6′-tri-N-benzyloxycarbonyl derivative by treatment with a suitable acylating agent such as N-(benzyloxycarbonyloxy)succinimide. The tri-N-benzyloxy intermediate is acylated with an activated carboxylic acid derivative to obtain a per-N-blocked 2-deoxy-4-N-acylfortimicin B derivative which is converted to a 2-deoxy-4-N-acylfortimicin B salt by catalytic hydrogenolysis in the presence of an acid.

2-Deoxy-4-N-alkylfortimicins B are prepared by treating a per-N-protected-2-deoxy-4-N-acylfortimicin B with a boron hydride reducing agent followed by subsequent removal of the N-protecting groups.

The corresponding 2′-N-acetyl and 2′-N-glycyl fortimicins B are readily prepared by rearrangement of corresponding 4-N-substituted fortimicins. In one method of preparation, the stable acid addition salts of the 4-N-substituted fortimicins are converted to the free bases by, for example, by use of a suitable anion exchange resin. The 2′-N-substituted fortimicins B are then prepared by placing the 4-N-substituted fortimicin free bases in water solution which readily rearranges the substituent on the nitrogen atom attached to $C_4$ to the nitrogen atom attached to $C_2$. Treatment of the 2′-N-substituted fortimicins B with suitable N-acylating agents such as N-(benzyloxycarbonyloxy)succinimide, benzyloxycarbonyl chloride or O-(benzyloxycarbonyl) p-nitrophenol in a solvent system such as N,N-dimethyl formamide-methanol-water results in the 1,6′-di-N-protected intermediate, i.e., 1,6′-di-N-benzyloxycarbonyl intermediates which can be acylated at the 4-N-position with a variety of activated carboxylic acid derivatives, such as a carboxylic acid anhydride, a carboxylic acid chloride, an active carboxylic acid ester, or a carboxylic acid azide.

The active esters may be conveniently prepared by reacting the appropriate carboxylic acid,

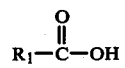

with, for example, 1-hydroxybenzotriazole, N-hydroxysuccinimide, or N-hydroxy-5-norborene-2,3-dicarboximide according to the method of M. Fujino et al., Chem. Pharm. Bull, Japan, 22 1857 (1974) wherein $R_1$ is an acyl group as defined in Formula I.

After completion of the N-acylation of the $C_4'$—N—methylamino group, it is necessary to remove the benzyloxycarboxyl protecting groups, most conveniently carried out by hydrogenolysis over a palladium on carbon catalyst. The fortimicin analogs thus prepared are conveniently isolated as the hydrochloride salts when the hydrogenolysis is carried out in the presence of a slight excess of hydrochloric acid.

The 2′-N-alkylfortimicins B are conveniently prepared by treatment of the 2′-N-acylfortimicins B with a suitable reducing agent such as diborane or a metal hydride such as lithium aluminum hydride. The resulting 2′-N-alkylfortimicins B derivative can then be treated with a suitable N-acylating agent as described above leaving the $C_4$-methylamino group free. $C_4$-N-acylation and deblocking as described previously gives the 2′-N-alkyl-4-N-acylfortimicins B.

The 4,2′-di-N-alkylfortimicins B are conveniently prepared by treating the desired N-protected 4,2′-di-N- acylfortimicin B with a suitable reducing agent, e.g., diborane. Deblocking by hydrogenolysis as described above gives 4,2'-di-N-alkylfortimicins B. Alternatively, the 4,2'-di-N-alkylfortimicins can be prepared by reduction of a suitable 2'-N-alkyl-4-N-acylfortimicin B. For example, a 2'-N-alkyl-4-N-acylfortimicin B or an N-protected 2'-N-alkyl-4-N-acylfortimicin B may be treated with a suitable reducing agent, e.g., diborane. In the case of the resulting N-protected 4,2'-di-N-alkylfortimicin B, the N-blocking groups can be conveniently removed by hydrogenolysis providing the 4,2'-di-N-alkylfortimicin B.

Alternatively, the 2-deoxy-2'-N-acyl derivatives of this invention can be prepared by reacting 2-deoxyfortimicin B with tert-butyl-S-(4,6-dimethyl-pyrimidin-2-yl)thiolcarbonate to obtain the 2'-tert-butyloxycarbonyl (Boc) fortimicin B intermediate.

The 2'-Boc-intermediate is then reacted with a suitable acylating agent, i.e., N-benzyloxycarbonyl)succinimide which results in the 1,6'-di-N-benzyloxycarbonyl-2'-Boc-fortimicin B intermediate. Treatment of the latter intermediate with an active ester of N-protected glycine, e.g., the hydroxysuccinimide ester of N-benzyloxycarbonylglycine in the presence of a suitable solvent system such as N,N-dimethylformamide-methanol-water results in the 2'-Boc-tri-N-benzyloxycarbonyl fortimicin A intermediate.

2-Alkylation or acylation is then conveniently accomplished by reacting the 2'-deprotected intermediate with a suitable aldehyde ($R_1CHO$) in the presence of sodium borohydride or by treatment with a carboxylic acid ester as described above. Deprotection is then completed by hydrogenolysis in the presence of 5% palladium on carbon catalyst which results in the desired 2'-alkyl or 2'-acyl derivatives.

The following examples further illustrate the present invention.

EXAMPLE 1

1,2',6'-Tri-N-benzyloxycarbonylfortimicin B

To a stirred solution of 2.0 g. of fortimicin B, 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-ammonium hydroxide (23.4:1.4:0.1 v/v/v) gave 1.05 g of 1,2',6'-tri-N-benzyloxycarbonylfortimicin B: $[\alpha]_D^{25} + 16.5°$ (C 1.0, $CH_3OH$); IR ($CDCl_3$) 1712 and 1507 cm$^{-1}$; NMR ($CDCl_3$)$\delta$ 1.03($C_6'$—$CH_3$, $J_{6',7'}$=6.0 Hz), 2.32 ($C_4$—$NCH_3$), 3.41 ($OCH_3$).

Anal. Calcd. for $C_{39}H_{50}N_4O_{11}$: C,62.39; H,6.71; N,7.46. Found: C,62.16; H,6.76; N,7.43.

EXAMPLE 2

1,2',6'-Tri-N-benzyloxycarbonyl-4,5-salicylaldehyde oxazolidine fortimicin B

A solution of 22 g of 1,2',6'-tri-N-benzyloxycarbonylfortimicin B in 396 ml of methanol is treated with 3.96 ml of salicylaldehyde and refluxed for 1 hour. Evaporation of the reaction mixture under reduced pressure gives 26 g of 1,2',6'-tri-N-benzyloxycarbonyl-4,5-salicylaldehyde oxazolidine fortimicin B as a brownish yellow solid:NMR ($CDCl_3$)$\delta$ 0.94($C_6'$—$CH_3$, $J_{6',7'}$=7.0 Hz), 2.34 ($C_4$—$NCH_3$), 3.49 ($C_3$—$OCH_3$), 7.31 (Cbz)

EXAMPLE 3

1,2',6'-Tri-N-benzyloxycarbonyl-4,5-(2-o-methanesulfonylsalicylaldehyde)-oxazolidine-2-o-methanesulfonylfortimicin B A stirring solution of 26 g of 1,2',6'-tri-N-benzyloxycarbonyl-4,5-salicylaldehyde oxazolidine fortimicin B in 154 ml of dry pyridine is treated with 12.26 ml of freshly distilled methanesulfonylchloride. After stirring for 20 hours, the reaction mixture is poured into 2000 ml of 5% sodium hydrogen carbonate solution and extracted 2 times with 1000 ml portions of chloroform. The combined chloroform extract is washed with 1000 ml of 5% sodium hydrogen carbonate and then twice with 1000 ml portions of water. The chloroform is evaporated under reduced pressure and the pyridine is removed by repeated codistillation with benzene to give 31.2 g of 1,2',6'-tri-N-benzyloxycarbonyl-4,5-(2-O-methanesulfonylsalicylaldehyde)-oxazolidine-2-O-methanesulfonyl fortimicin B: NMR($CDCl_3$)$\delta$ 1.0 ($C_6'$—$CH_3$, $J_{6',7'}$=7.0 Hz), 2.19 ($C_4$—$NCH_3$), 2.94 ($C_2$—$OSO_2CH_3$), 3.15 (Ar—$OSO_2CH_3$), 3.60 ($C_3$—$OCH_3$), 7.33 (Cbz).

EXAMPLE 4

1,2',6'-Tri-N-benzyloxycarbonyl-2-O-methanesulfonylfortimicin B

A stirring solution of 31.2 g of 1,2',6'-tri-N-benzyloxycarbonyl-4,5-(2-O-methanesulfonylsalicylaldehyde) oxazolidine-2-O-methanesulfonylfortimicin B in 1000 ml of tetrahydrofuran is treated with 262 ml of 0.4 N hydrochloric acid. After stirring for 4 hours, the reaction mixture is poured into 5700 ml of 6 N ammonium hydroxide solution and extracted 2 times with 1400 ml portions of chloroform. The combined chloroform extract is washed with 5700 ml of 7% sodium hydrogen sulfite solution and then 2 times with 1180 ml portions of water. Removal of the chloroform under reduced pressure gives 27.35 g of crude 1,2',6'-tri-N-benzyloxycarbonyl-2-O-methanesulfonylfortimicin B. The crude material is chromatographed on a column (29×50) of Sephadex LH-20 gel prepared and eluted with 95% ethanol. Fractions containing the desired material are combined and concentrated to dryness under reduced pressure to give pure 1,2',6'-tri-N-benzyloxycarbonyl-2-O-methanesulfonylfortimicin B as a glass: $[\alpha]_D^{23} + 18.5°$ (c 1.0, $CH_3OH$); IR ($CDCl_3$) 3436, 3350, 1703, 1502, 1354 and 1173 cm$^{-1}$; NMR ($CDCl_3$)$\delta$ 1.07 ($C_6'$—$CH_3$, $J_{6',7'}$=7.0 Hz), 2.34($C_4$-$NCH_3$), 2.87 ($OSO_2CH_3$), 3.48 ($OCH_3$).

Anal. Calcd. for $C_{40}H_{52}N_4O_{13}S$: C,57.96; H,6.32; N,6.76. Found: C,57.65; H,6.52; N,6.62.

EXAMPLE 5

2-O-Methanesulfonylfortimicin B Tetrahydrochloride

A solution of 4.42 g of 1,2',6'-tri-N-benzyloxycarbonyl-2-O-methanesulfonylfortimicin B in 310 ml of 0.2 N hydrochloric acid in methanol is treated for 4 hours with 4.5 g of 5% palladium on carbon under hydrogen and 3 atmospheres of pressure. The catalyst is filtered off and washed with ethanol. The filtrate is concentrated to dryness under reduced pressure and the excess hydrochloric acid is removed by repeated codistillation with methanol to leave 2.79 g of 2-O-methanesulfonylfortimicin B tetrahydrochloride as a white glass: $[\alpha]_D^{25}$ +91.7° (c 1.01, CH$_3$OH); IR (KBr) 3400, 2920, 1590, 1330 and 1165 cm$^{-1}$; NMR (D$_2$O)δ 1.82 (C$_{6'}$—CH$_3$, J$_{6',7'}$=7.0 Hz), 3.31 (C$_4$—NCH$_3$), 3.88 (C$_2$OSO$_2$CH$_3$), 407 (C$_3$—OCH$_3$), 5.88 (C$_6$·H, J=4.0 Hz).

EXAMPLE 6

1,2-Epiminofortimicin B

A solution prepared from 2.8 g of 2-O-methanesulfonylfortimicin B tetrahydrochloride in 20 ml of water is passed through a column (2.2×20 cm) of an anion exchange resin quaternary ammonium styrene type, e.g., AG ® 2-X8, 500 mesh resin (OH) sold by Bio-Rad Laboratories, sufficient to remove the chloride ion. Basic elutes are combined and allowed to stand at room temperature for 72 hours. Evaporation of the water under reduced pressure leaves 3.0 g of 1,2-epiminofortimicin B: NMR (D$_2$O)δ 1.55 (C$_{6'}$—CH$_3$, J=7.0 Hz), 2.83 (C$_4$—NCH$_3$), 4.02 (C$_3$—OCH$_3$), 5.42 (C$_1$,H,J=3.0 Hz).

EXAMPLE 7

2-Deoxyfortimicin B and 1-Deamino-2-deoxy-2-epi-aminofortimicin B

A solution prepared from 3.22 g of 1,2-epiminofortimicin B in 250 ml of wet ethanol is treated for 24 hours with 12 g of Raney nickel under 3 atmospheres of hydrogen. The catalyst is collected on a filter and washed with ethanol. The filtrate is concentrated to dryness under reduced pressure to give 2.90 g of a mixture of 2-deoxyfortimicin B and 1-deamino-2-deoxy-2-epi-aminofortimicin B as a white froth. The mixture is chromatographed on a column (2.9×50 cm) of a cation exchange resin, NH$_4^+$ form (e.g., Bio Rad 70, 100–200 mesh, carboxylic styrene type resin sold by Bio-Rad Laboratories) and eluted with a gradient of water to 1 N ammonium hydroxide. The first elutes are taken to dryness under reduced pressure to yield 1.347 g of pure 2-deoxyfortimicin B: NMR (D$_2$O)δ 1.5 (C$_{6'}$—CH$_3$, J=7.0 Hz), 2.82 (C$_4$NCH$_4$), 3.86 (C$_3$OCH$_3$), 5.48 (C$_1$,H,J=3.5 Hz)

Later elutes are collected and taken to dryness under reduced pressure to yield 1.172 g of 1-deamino-2-deoxy-2-epiaminofortimicin B: NMR (D$_2$O)δ 1.51 (C$_{6'}$,CH$_3$, J=7.0 Hz), 2.83 (C$_4$—NCH$_3$), 4.02 (C$_3$—OCH$_3$), 5.31 (C$_1$,H,J=4.0 Hz).

EXAMPLE 8

1,2',6'-Tri-N-benzyloxycarbonyl-2-deoxyfortimicin B

A stirring, ice-bath cooled solution of 0.843 g of 2-deoxyfortimicin B in 12.6 ml of water and 25.3 ml methanol is treated with 2.09 g of N-(benzyloxycarbonyloxy)succinimide. After stirring in the cold for 3 hours and then at room temperature for 20 hours, the major portion of the methanol is evaporated under reduced pressure. After addition of 90 ml of water, the product is extracted with 180 ml of chloroform. The aqueous portion is extracted 2 more times with 60 ml portions of chloroform. The combined chloroform extract is washed with water and dried over anhydrous magnesium sulfate. Evaporation under reduced pressure gives a foam which is chromatographed on a column (2.3×70 cm) of silica gel prepared and eluted with a solvent system consisting of chloroform-methanol-ammonium hydroxide (23.4:1.4:0.1 v/v/v). Fractions containing the desired material are collected and evaporated to dryness under reduced pressure to give 0.936 g of 1,2',6'-tri-N-benzyloxycarbonyl-2-deoxyfortimicin B as a colorless froth: NMR (D$_2$O)δ 1.12 (C$_{6'}$,H$_3$,J$_{6',7'}$=6.0 Hz) 2.26 (C$_4$—NCH$_3$), 3.29 (C$_3$—OCH), 4.78 (C$_1$,H, J=4.0 Hz), 7.31 (Cbz).

EXAMPLE 9

Tetra-N-benzyloxycarbonyl-2-deoxyfortimicin A

A stirring solution of 0.807 g of 1,2',6'-tri-N-benzyloxycarbonyl-2-deoxyfortimicin B in 14 ml of dry tetrahydrofuran is treated for 18 hours with 0.439 g of the N-hydroxysuccinimide ester of N-benzyloxycarbonylglycine. The tetrahydrofuran is evaporated under reduced pressure to give 1.231 of colorless froth. The froth is chromatographed on a column (2.0×44 cm) of silica gel prepared and eluted with a solvent system consisting of benzene-methanol-95% ethanol-ammonium hydroxide (23.5:1.5:1.9:0.2 v/v/v/v). Fractions containing 1,4,2',6'-tetra-N-benzyloxycarbonyl-2-deoxyfortimicin A are taken to dryness under reduced pressure and rechromatographed on a column of Sephadex LH-20 gel prepared and eluted with 95% ethanol. Elutes containing the major product are evaporated to give 0.623 g of tetra-N-benzyloxycarbonyl-2-deoxyfortimicin A: NMR(CDCl$_3$)δ 1.17 (C$_{6'}$—CH$_3$) 2.86 (C$_4$—NCH$_3$), 3.26 (C$_3$—OCH$_3$), 4.83 (C$_1$,H, J=4.0 Hz), 7.3 (Cbz).

EXAMPLE 10

2-Deoxyfortimicin A Tetrahydrochloride

A solution of 0.463 g of tetra-N-benzyloxycarbonyl-2-deoxyfortimicin A in 60 ml of 0.2 N hydrochloric acid in methanol is treated for 4 hours with 0.463 g of 5% palladium on carbon under 3 atmospheres of hydrogen. The catalyst is collected on a filter and washed with several small portions of methanol. The filtrate is evaporated to dryness under reduced pressure to give a white solid. Excess hydrochloric acid is removed by repeated co-distillation with methanol to leave 0.305 g of 2-deoxyfortimicin A tetrahydrochloride: NMR (D$_2$O)δ 1.79 (C$_{6'}$—CH$_3$, J=7.0 Hz), 3.58 (C$_4$—NCH$_3$), 3.90 (C$_3$—OCH$_3$), 5.82 (C$_1$,H, J=4.0 Hz).

EXAMPLE 11

Tetra-N-benzyloxycarbonyl-2-deoxy-4-(β-aminoethyl)fortimicin B

A stirring solution of 1.0 g of tetra-N-benzyloxycarbonyl-2-deoxyfortimicin A in 16 ml of dry tetrahydrofuran purged with nitrogen is treated with 1.0 M diborane (3.0 ml) in tetrahydrofuran. After stirring in a nitrogen atmosphere for 4 hours an additional 2.0 ml of 1.0 M diborane in tetrahydrofuran is added and stirring is continued for another 2 hours. After the cautious addition of water to destroy excess diborane, the reaction mixture is taken to dryness under reduced pressure. Boric acid is removed by repeated co-distillation with methanol to give crude tetra-N-benzyloxycarbonyl-2-deoxy-4-N-(β-aminoethyl)fortimicin B. The crude material is chromatographed on a column of silica gel prepared and eluted with a solvent system consisting of benzene-methanol-95% ethanol-ammonium hydroxide (23.5:1.5:1.9:0.2 v/v/v/v). Elutes containing the major product are collected and evaporated to dryness to give tetra-N-benzyloxycarbonyl-2-deoxy-4-N(β-aminoethyl)fortimicin B.

EXAMPLE 12

2-Deoxy-4-N-(β-aminoethyl)fortimicin B pentahydrochloride

A solution prepared from 1 g of tetra-N-benzyloxycarbonyl-2-deoxy-4-N-(β-aminoethyl)fortimicin B and 180 ml of 0.2 N hydrochloric acid in methanol is treated for 4 hours with 5% palladium on carbon under 3 atmospheres of hydrogen. The catalyst, removed by filtration through a celite mat, is washed with additional methanol. The combined filtrates are taken to dryness under reduced pressure to give a white solid. Excess hydrochloric acid is removed by repeated co-distillation with methanol to give 2-deoxy-4-N-(β-aminoethyl)fortimicin B pentahydrochloride.

EXAMPLE 13

1,2',6'-Tri-N-Salicylidene-4,5-Salicylaldehyde Oxazolidine Fortimicin B

A solution of 2.0 g of fortimicin B in 16 ml of methanol is treated with 0.24 ml of salicylaldehyde and refluxed for 1 hour. Evaporation of the reaction mixture under reduced pressure gives 4.563 g of 1,2',6'-tri-N-salicylidene-4-5-salicylaldehyde oxazolidine fortimicin B as a froth: NMR (CDCl$_3$)δ 1.09 (C$_6$'—CH$_3$,), 2.37 (C$_4$—NCH$_3$), 3.5 (C$_3$—OCH$_3$), 5.24 (C$_1$, $\underline{H}$) 8.14, 8.28, 8.40 (—N=CH—C$_6$H$_6$O).

EXAMPLE 14

1,2',6'-Tri-N-(2-$\underline{O}$-methanesulfonylsalicylidene)-4,5-(2-$\underline{O}$-methanesulfonylsalicylaldehyde)-oxazolidine-2-O-methanesulfonylfortimicin B A stirring solution of 1.0 g of 1,2',6'-tri-N-salicylidene-4,5-salicylaldehyde oxazolidine fortimicin B in 5.9 ml of dry pyridine is treated with 0.6 ml of freshly distilled methanesulfonylchloride. After stirring for 3 hours the reaction mixture is poured into 100 ml of 5% sodium hydrogen carbonate solution. The solution is extracted 2 times with 50 ml portions of chloroform. The combined chloroform extract is washed with 50 ml of 5% sodium hydrogen carbonate solution and then 2 times with 25 ml portions of water. The chloroform is evaporated under reduced pressure and the residual pyridine is removed by repeated co-distillations with benzene to give 1.349 g of 1,2',6'-tri-N-(2-O-methanesulfonylsalicylidene)-4,5-(2-O-methanesulfonylsalicylaldehyde)-oxazolidine-2-$\underline{O}$-methanesulfonylfortimicin B: NMR (CDCl$_3$)δ 0.98 (C$_6$'—CH$_3$), 7.18 (C$_4$—NCH$_3$).

EXAMPLE 15

2-O-Methanesulfonylfortimicin B Tetrahydrochloride

A stirring solution of 1.34 g of 1,2',6'-tri-N-(2-O-methanesulfonylsalicylidene)-4,5-(2-$\underline{O}$-methanesulfonylsalicylaldehyde)-oxazolidine-2-$\underline{O}$-methanesulfonylfortimicin B in 44 ml of tetrahydrofuran is treated with 11.1 ml of 0.4 N hydrochloric acid. After stirring for 4 hours the reaction mixture was extracted 3 times with 50 ml portions of chloroform which are discarded. The aqueous layer is taken to dryness to give 0.556 g of 2-O-methanesulfonylfortimicin B tetrahydrochloride.

EXAMPLE 16

2-Deoxy-2'-N-glycylfortimicin B

An aqueous solution of 10.0 g of 2-deoxyfortimicin A disulfate is passed through a column of an anion exchange resin, quaternary ammonium styrene type, e.g., Bio-Rad Laboratories, AG® 2-X8, 100–200 mesh, hydroxyl form, sufficient to remove the sulfate ion. The basic elutes are collected and diluted with water to a 1% solution based on starting fortimicin A disulfate. After standing at 37° C. for 20 days the water is evaporated under reduced pressure to leave an oil. A 2.07 g portion of the oil is chromatographed on a column (2.2×52 cm) of a cation exchange resin, carboxylic type, e.g., Bio-Rad Laboratories, Bio-Rex 70, 100–200 mesh, ammonium form and eluted with 0.1 N ammonium hydroxide. Elutes containing and 2-deoxy-2'-glycylfortimicin B are collected, evaporated to a small volume under reduced pressure and lyophilized to give the desired product.

EXAMPLE 17

2-Deoxy-2'-N-(benzyloxycarbonylglycyl)-1,6'-di-N-benzyloxycarbonylfortimicin B A stirred solution of 0.333 g of 2-deoxy-2'-N-glycylfortimicin B in 4.5 ml of water and 9.0 ml of methanol cooled to 4° C. in an ice bath, is treated with 0.666 g of benzyloxycarbonyloxysuccinimide. Stirring is continued at 4° C. for 3 hours and then at room temperature for 20 hours. The resulting solution is concentrated under reduced pressure to an oil. The oil is shaken with a mixture of 150 ml of chloroform and 75 ml of water. The chloroform layer is separated and washed with 75 ml of water. The aqueous portions are washed in series with two 75 ml portions of chloroform. The chloroform solutions are combined and dried over anhydrous magnesium sulfate. Evaporation of the chloroform under reduced pressure leaves 0.596 g of product. The product is chromatographed on a column (1.8×48 cm) of silica gel prepared and eluted with a solvent system consisting of chloroform methanol-ammonium hydroxide (23.4: 1.4:0.1 v/v) to yield the desired 2-deoxy-2'-N-(N-benzyloxycarbonylglycyl)-1,6'-di-N-benzyloxycarbonylfortimicin B.

EXAMPLE 18

2-Deoxy-tetra-N-benzyloxycarbonyl-2'-N-glycylfortimicin A

To a stirred solution of 0.234 g of 2-deoxy-2'-N-(N-benzyloxycarbonylglycyl)-1,6'-di-N-dibenzyloxycarbonylfortimicin B, 0.105 g of N-benzyloxycarbonylglycine and 0.939 g. of 1-hydroxybenzotriazole monohydrate in 2.0 ml tetrahydrofuran is added 0.087 g of N,N-dicyclohexylcarbodiimide in 2.0 ml of tetrahydrofuran. Stirring is continued for 20 hours at room temperature. Insoluble dicyclohexylurea is removed by filtration and the filtrate is concentrated to dryness under reduced pressure to give 0.408 g of lemon-yellow solid. The solid is chromatographed on a column (1.8×42 cm) of silica gel eluted with a solvent system consisting of benzene-methanol-95% ethanol-ammonium hydroxide (23.5:1.4:2.0:0.2 v/v/v/v) to about 0.24 g of 2-deoxy-tetra-N-benzyloxycarbonyl-2'-glycylfortimicin A.

EXAMPLE 19

2-Deoxy-2'-N-glycylfortimicin A tetrahydrochloride

A solution of 0.235 g of the above 2-deoxy-tetra-N-benzyloxycarbonyl-2'-N-glycylfortimicin A in 40 ml of 0.2 N hydrochloric acid in methanol is hydrogenolyzed for 4 hours under 3 atmospheres of hydrogen in the presence of 0.235 g of 5% palladium on carbon. The catalyst is removed by filtration through a celite mat.

The filtrate is concentrated to dryness and excess hydrochloric acid is removed by repeated co-distillation with methanol under reduced pressure to give 2-deoxy-N-glycylfortimicin A tetrahydrochloride.

EXAMPLE 20

2-Deoxy-1,2',6'-tri-N-benzyloxycarbonylfortimicin B

To a stirred solution of 2.0 g of 2-deoxyfortimicin B, 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromotographed on silica gel. Elution with a solvent system composed of chloroform-methanol-ammonium hydroxide (23.4:1.4:0.1 v/v/v) gave 2-deoxy-1,2',6'-tri-N-benzyloxycarbonylfortimicin B.

EXAMPLE 21

2-Deoxy-1,2',6'-tri-N-benzyloxycarbonyl-4-N-acetylfortimicin B

To a stirred solution of 3.22 g of 2-deoxy-1,2',6'-tri-N-benzyloxycarbonylfortimicin B in 225 ml of methanol, cooled in an ice bath, is added 16 ml of acetic anhydride over a 15 minute period. Stirring is continued at 0° for 2 hours and then at room temperature for 2 hours. The methanol is evaporated under reduced pressure and residual acetic anhydride and acetic acid are removed by co-distillation with benzene and methanol to leave 3.0 g of 2-deoxy-1,2',6'-tri-N-benzyloxycarbonyl-4-N-acetylfortimicin B.

EXAMPLE 22

2-Deoxy-4-N-acetylfortimicin B trihydrochloride

A solution of 1.0274 g of the above 2-deoxy-tri-N-benzyloxycarbonyl-4-N-acetylfortimicin B in 180 ml of 0.2 N hydrochloric acid in methanol is hydrogenolyzed over 1.2 g of 5% palladium on carbon for 4 hours. The catalyst is removed by filtration through a celite mat. The filtrate is concentrated to dryness under reduced pressure and excess hydrochloric acid is removed by repeated co-distillation with methanol under reduced pressure to give 0.65 g of 2-deoxy-4-N-acetylfortimicin B trihydrochloride.

EXAMPLE 23

2-Deoxy-2'-N-acetylfortimicin B

An aqueous solution of 0.840 g of 2-deoxy-4-N-acetylfortimicin B trihydrochloride is passed through a column (1.1×19 cm) of an anion exchange resin, quaternary ammonium styrene type, e.g., Bio-Rad Laboratories, AG® 2-X8, 50–100 mesh, hydroxyl form, sufficient to remove the chloride ion. The basic eluates are collected and diluted to 84 ml with water. After standing at room temperature for 20 days the solution is evaporated under reduced pressure to a small volume and chromatographed on a column of a cation exchange resin, carboxylic type, e.g., Bio-Rad Laboratories, Bio-Rex 70, 100–200 mesh, ammonium form. Elution with a gradient of water to 1 N ammonium hydroxide gives fractions containing only 2-deoxy-2'-N-acetylfortimicin B. These fractions are concentrated to dryness under reduced pressure to give 0.390 g of the desired product.

EXAMPLE 24

2-Deoxy-1,6'-di-N-benzyloxycarbonyl-2'-N-acetylfortimicin B

A stirring solution of 0.290 g of 2-deoxy-2'-N-acetylfortimicin B in 4.5 ml of water and 9.0 ml of methanol, cooled to 0° in an ice bath, is treated with 0.388 g. of N-(benzyloxycarbonyloxy)succinimide. Stirring is continued at 0° for 3 hours and then at room temperature for 22 hours. The solution is concentrated under reduced pressure on an oil which is shaken with a mixture of 100 ml of chloroform and ↓ ml of water. The chloroform layer is separated and the aqueous portion is shaken with an additional 100 ml of chloroform. The combined chloroform solutions are washed two times with water and dried over anhydrous magnesium sulfate. Evaporation of the chloroform under reduced pressure leaves 0.480 g of colorless solid. The solid is chromatographed on a column (2.0×43 cm) of silica gel prepared and eluted with a solvent system consisting of chloroform, methanol, ammonium hydroxide (23.4:1.4:01 v/v/v) to give 2-deoxy-1,6'-di-N-benzyloxycarbonyl-2'-N-acetylfortimicin B.

EXAMPLE 25

2-Deoxy-tri-N-benzyloxycarbonyl-2'-N-acetylfortimicin A

To a stirred solution of 0.150 g of 2-deoxy-1,6'-di-N-benzyloxycarbonyl-2'-N-acetylfortimicin B, 0.065 g of N-benzyloxycarbonylglycine and 0.074 g of 1-hydroxybenzotriazole monohydrate in 2.0 ml of tetrahydrofuran is added a solution of 0069 g of N,N'-dicyclohexylcarbodiimide in 2.0 ml of tetrahydrofuran. Stirring is continued at room temperature for 23 hours. The precipitated N,N'-dicyclohexylurea is removed by filtration. The filtrate is evaporated under reduced pressure and the residue is chromatographed on a column of silica gel, prepared and eluted with a solvent system consisting of benzene-methanol-95% ethanol-ammonium hydroxide (23.5:1.4:2. 0:0.2 v/v). Fractions containing the desired product are taken to dryness under reduced pressure leaving 2-deoxy-tri-N-benzyloxycarbonyl-2'-N-acetylfortimicin A.

EXAMPLE 26

2-Deoxy-2'-N-acetylfortimicin A trihydrochloride

A solution of 0.178 g of 2-deoxy-tri-N-benzyloxycarbonyl-2'-N-acetylfortimicin A in 30 of 0.2 N hydrochloric acid in methanol is hydrogenolyzed for 4 hours under 3 atmospheres of hydrogen in the presence of 0.178 g of 5% palladium on carbon. The catalyst is removed by filtration through a celite mat. The filtrate is concentrated to a small volume and treated with activated carbon, e.g., Darco® G-60, Atlas Chemical Industries, Inc. The carbon is removed by filtration through a celite mat. The filtrate is concentrated to dryness and excess hydrochloric acid is removed by repeated co-distillation with methanol under reduced pressure to give the desired product.

EXAMPLE 27

2-Deoxy-2'-N-($\beta$-aminoethyl)fortimicin B

A stirring solution of 2.0 g of 2-deoxy-2'-N-glycylfortimicin B in 80 ml of tetrahydrofuran is treated with 1.22 g of lithium aluminum hydride. The stirring reaction mixture is refluxed for 20 hours and then the excess lithium aluminum hydride is consumed by the careful addition of water. The insoluble material is sedimented by centrifugation. The pellet is suspended in 50 ml. of water and centrifuged. The combined supernatants are taken to dryness under reduced pressure to give 1.44 g of brown solid. The solid is chromatographed on a column (2.0×40 cm) of cation exchange resin, carboxylic type, e.g., Bio-Rad Laboratories, Bio-Rex 70, 100–200 mesh, ammonia form, and eluted with a gradient of water to 1 N ammonium hydroxide. Fractions containing the desired product are concentrated to a small volume and lyophilized to give 0.8 g of 2-deoxy-2'-N-(β-aminoethyl)fortimicin B:

EXAMPLE 28

2-Deoxy-1,6'-di-N-benzyloxycarbonyl-2'-N-[N-benzyloxycarbonyl(β-aminoethyl)]fortimicin B A stirred solution of 0.824 g of 2-deoxy-2'-N-(β-aminoethyl)fortimicin B in 12.4 ml of water and 24.8 ml of methanol cooled to 4° in an ice bath, is treated with 1.83 g of N-(benzyloxycarbonyloxy)succinimide. Stirring is continued at 4° for 3 hours and then at room temperature for 22 hours. The reaction mixture is concentrated to an oil under reduced pressure and then it is shaken with a mixture of 150 ml of chloroform and 75 ml of water. The chloroform layer is separated and washed with 75 ml of water. The aqueous portions are then washed in series with two 80 ml portions of chloroform. The combined chloroform solution is dried over anhydrous magnesium sulfate and concentrated to dryness under reduced pressure to give 1.584 g of colorless solid. The solid is chromatographed on a column (2.2×65 cm) of silica gel prepared and eluted with a solvent system consisting of benzene-methanol-95% ethanol-ammonium hydroxide (23.5:1.4:2.0:0.2 v/v/v/v) to give a 0.58 g of 2-deoxy-1,6'-di-N-benzyloxycarbonyl-2'-N-[N-benzyloxycarbonyl(β-aminoethyl)]fortimicin B.

EXAMPLE 29

2-Deoxy-1,6-di-N-benzyloxycarbonyl-2'-N-[N-benzyloxycarbonyl-(β-aminoethyl)]-4-N-(N-benzyloxycarbonylglycyl)fortimicin A A stirred solution of 0.503 g of 2-deoxy-tri-N-benzyloxycarbonyl-2'-N-[N-benzyloxycarbonyl(β-aminoethyl)]-fortimicin B in 3.4 ml of tetrahydrofuran is treated with 0.223 g of the N-hydroxysuccinimide ester of N-benzyloxycarbonylglycine. After stirring for 20 hours at room temperature the tetrahydrofuran is evaporated under reduced pressure to leave 0.714 g of colorless solid. The solid is chromatographed on a column (1.5×74 cm) of silica gel eluted with a solvent system consisting of benzene-methanol-95% ethanol-ammonium hydroxide (23.5:1.4:2.0:0.2 v/v/v/v) to give 0.405 g of 2-deoxy-1,6'-di-N-benzyloxycarbonyl-2'-N-[N-benzyloxycarbonyl(β-aminoethyl)]-4-N-(N-benzyloxycarbonylglycyl)fortimicin A.

EXAMPLE 30

2-Deoxy-2'-N-(β-aminoethyl)fortimicin A pentahydrochloride

A solution of 0.426 g of 2-deoxy-1,6'-di-N-benzyloxycarbonyl-2'-N-[N-benzyloxycarbonyl(β-aminoethyl)]-4-N-(N-benzyloxycarbonylglycyl)fortimicin B in 70 ml of 0.2 N methanolic hydrochloric acid is hydrogenolyzed over 0.40 g of 5% palladium on carbon for 4 hours. The catalyst, collected by filtration through a celite mat, is washed with several small portions of methanol. The filterate is evaporated to dryness under reduced pressure. Excess hydrochloric acid is removed by repeated co-distillation with methanol under reduced pressure to give 0.268 g of 2-deoxy-2'-N-(β-aminoethyl)fortimicin A pentahydrochloride.

The in vitro antibiotic activities of the compounds of this invention are determined by a two-fold dilution test using Mueller-Hinton agar, 10 ml per Petri plate. The inoculum of approximately $1 \times 10^5$ of the indicated test organism is delivered by the Steer's replicator. The test is incubated at 37° C. for 24 hours.

The compounds of this invention are active as systemic antibiotics when injected by parenteral routes of administration, i.e., by the intramuscular, intraveneous, intraperitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 1 to 100 mg/kg of body weight daily are administered to a mam-

We claim:
1. A compound of the formula:

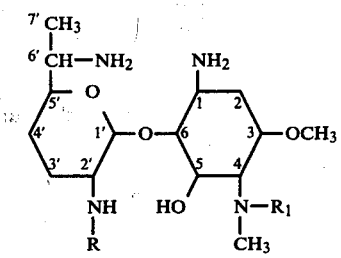

wherein: R is acyl, aminocyl, N-monoloweralkylaminoacyl, N,N-diloweralkylaminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, or N,N-diloweralkylaminohydroxyloweralkyl; and $R_1$ is acyl, aminocyl, N-monoloweralkylaminoacyl, N,N-diloweralkylaminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen and wherein acyl is represented by the formula

Y being loweralkyl; and the pharmaceutically acceptable salts thereof.

2. A compound of claim 1 wherein $R_1$ is hydrogen.
3. A compound of claim 2: 2-deoxy-2'-N-glycylfortimicin B or a pharmaceutically acceptable salt thereof.
4. A compound of claim 2: 2-deoxy-2'-N-acetylfortimicin B, or a pharmaceutically acceptable salt thereof.
5. A compound of claim 2: 2-deoxy-2'-N-($\beta$-aminoethyl)fortimicin B or a pharmaceutically acceptable salt thereof.
6. A compound of claim 1 wherein both R and $R_1$ are an amino acid residue.
7. A compound of claim 6: 2-deoxy-2'-N-glycylfortimicin A or a pharmaceutically acceptable salt thereof.
8. A compound of claim 1 wherein R is aminoloweralkyl.
9. A compound of claim 1 wherein R is loweralkyl.
10. A compound of claim 1 wherein R is acyl.
11. A compound of claim 1 wherein R is amino acid residue.
12. A pharmaceutical composition comprising a compound of claim 1 and a pharmaceutically acceptable carrier or diluent.

* * * * *